(12) United States Patent
Wright

(10) Patent No.: US 9,248,315 B2
(45) Date of Patent: Feb. 2, 2016

(54) TARGETING METHOD FOR MICROBEAM RADIOSURGERY

(75) Inventor: Michael Dean Wright, Palo Alto, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 0 days.

(21) Appl. No.: 13/603,090

(22) Filed: Sep. 4, 2012

(65) Prior Publication Data
US 2014/0061511 A1    Mar. 6, 2014

(51) Int. Cl.
*A61N 5/10*    (2006.01)

(52) U.S. Cl.
CPC ............ *A61N 5/1042* (2013.01); *A61N 5/1045* (2013.01)

(58) Field of Classification Search
CPC ............ G21K 5/00; G21K 1/06; G21K 1/02; A61N 5/10; A61N 5/00; A61N 5/02; A61N 2/00; G01N 23/201; H05G 1/02; A61B 18/04; A61B 17/52; H01J 29/46
USPC .......... 378/64, 65, 88, 149, 193, 84; 600/1, 2, 600/9, 10, 11, 400, 407, 425, 426; 606/34; 250/492.3, 505.1
See application file for complete search history.

(56) References Cited

U.S. PATENT DOCUMENTS

| | | | |
|---|---|---|---|
| 5,192,869 A * | 3/1993 | Kumakhov | 250/505.1 |
| 5,339,347 A | 8/1994 | Slatkin et al. | |
| 5,825,847 A | 10/1998 | Ruth et al. | |
| 6,035,015 A | 3/2000 | Ruth et al. | |
| 6,678,348 B1 * | 1/2004 | Kumakhov | 378/84 |
| 7,158,607 B2 * | 1/2007 | Dilmanian et al. | 378/64 |
| 7,194,063 B2 | 3/2007 | Dilmanian et al. | |
| 7,242,748 B2 | 7/2007 | Loewen et al. | |
| 7,277,526 B2 | 10/2007 | Rifkin et al. | |
| 7,295,653 B2 | 11/2007 | Loewen et al. | |
| 7,301,972 B2 | 11/2007 | Loewen et al. | |
| 7,643,610 B2 * | 1/2010 | Dilmanian | 378/65 |
| 2008/0132886 A1 * | 6/2008 | Cohen et al. | 606/34 |

OTHER PUBLICATIONS

Dilmanian et al., "Tissue-Sparing Effect of X-Ray Microplanar Beams Particularly in the CNS: Is a Bystander Effect Involved?", Experimental Hematology, vol. 35, 2007, pp. 69-77; 9 pages.
Dilmanian et al., "Interlaced X-Ray Microplanar Beams: A Radiosurgery Approach With Clinical Potential", Proceedings of the National Academy of Sciences (PNAS), vol. 103, No. 25 Jun. 20, 2006; 6 pages.
K. J. Weeks, "The Compton Backscattering Process and Radiotherapy", Med. Phys. 24 (3), Mar. 1997; 7 pages.
Article title "First Trial of Spatial and Temporal Fractionations of the Delivered Dose Using Synchrontron Microbeam Radiation Therapy" published in the Journal of Synchrontron Radiation on Jan. 7, 2009.

* cited by examiner

*Primary Examiner* — William Thomson
*Assistant Examiner* — Victor Shapiro
(74) *Attorney, Agent, or Firm* — Vedder Price, P.C.

(57) ABSTRACT

A method of performing microbeam radiosurgery on a patient whereby opposing portions of target tissue within a patient are exposed to a flux of high energy quanta via microbeam envelopes. The microbeam envelopes are applied in multiple non-parallel orientations such that the exposed portions of the target tissue define a substantially closed volume. The tissue remaining inside is thereby denied blood flow and dies.

22 Claims, 10 Drawing Sheets

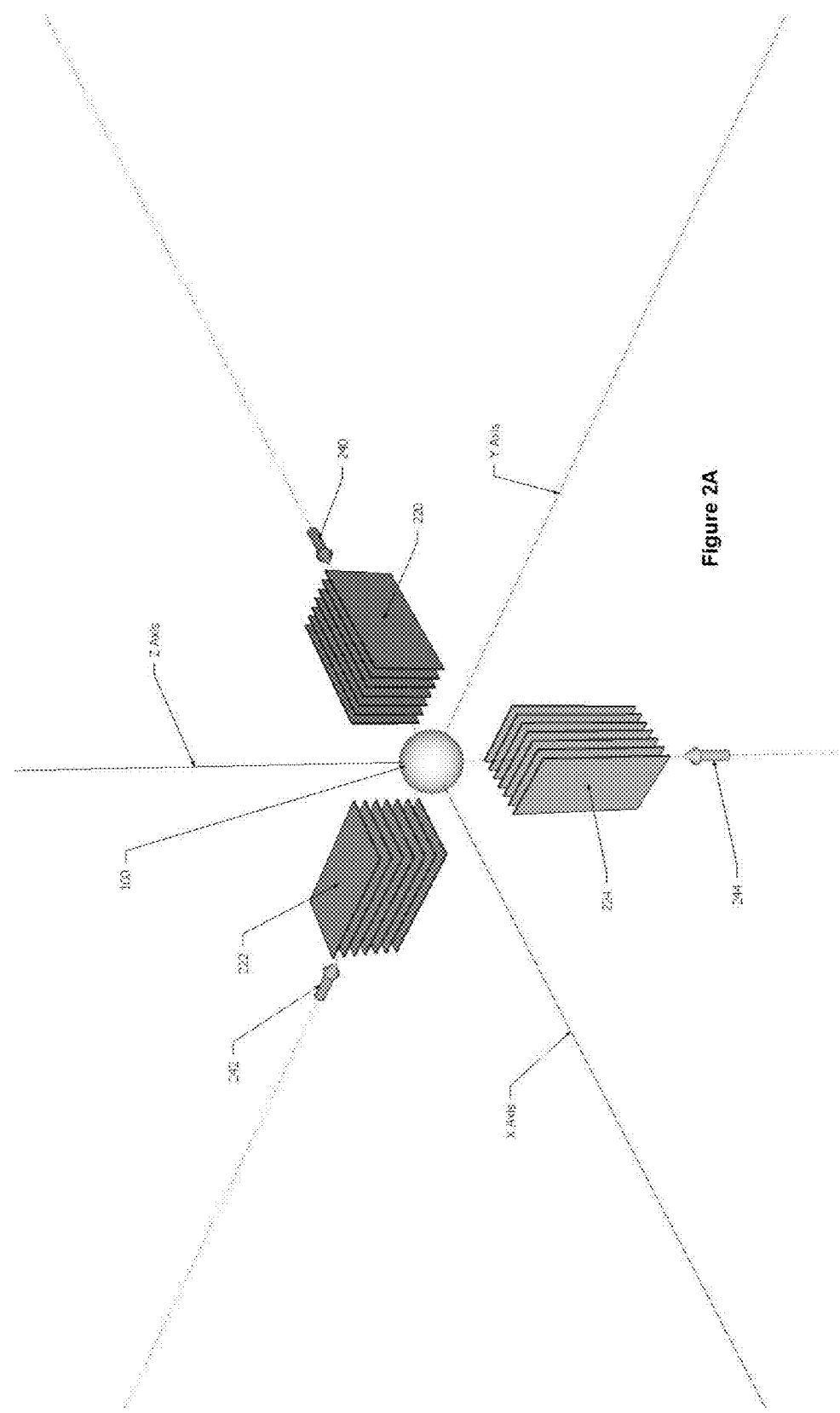

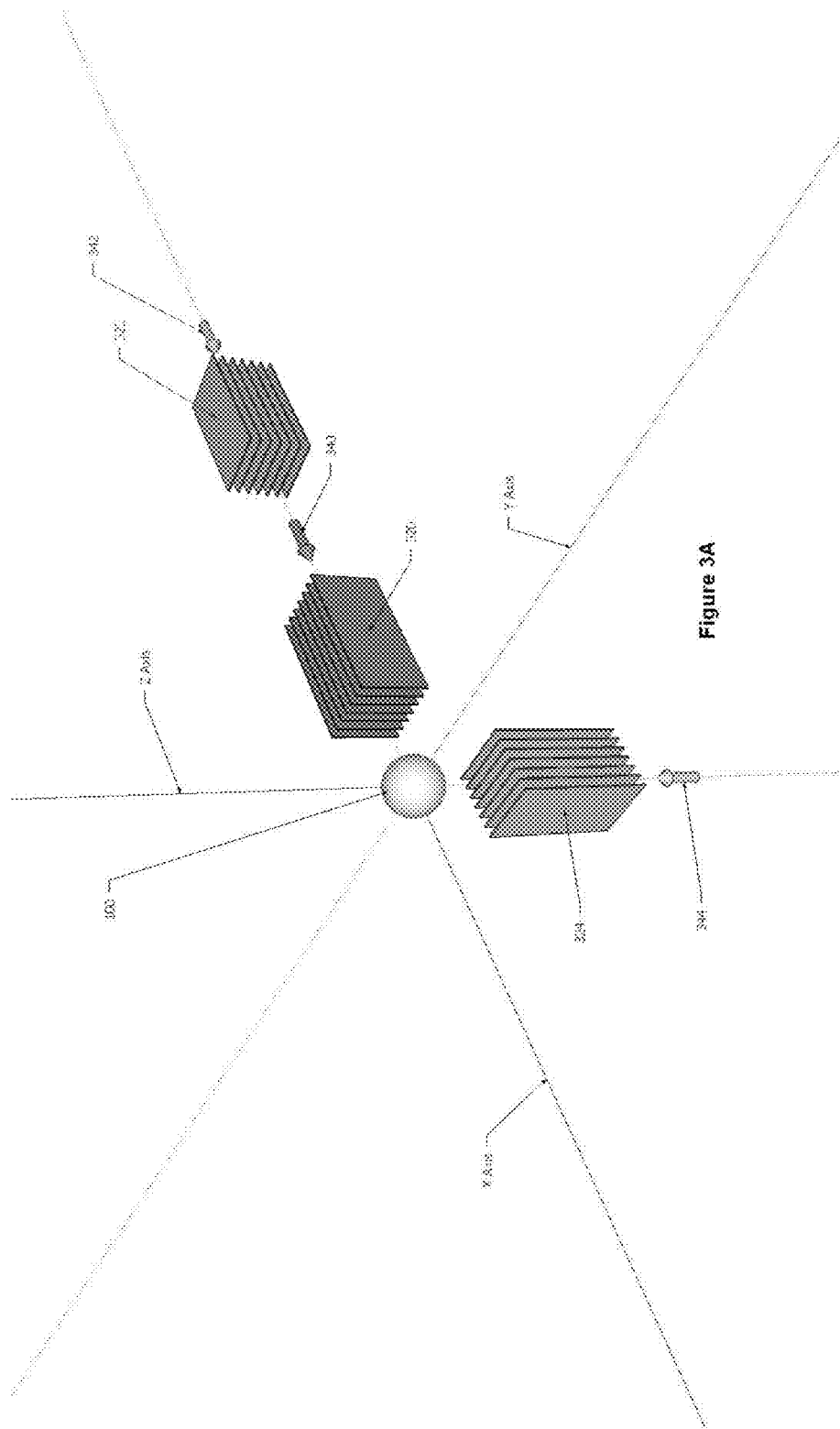

US 9,248,315 B2

TARGETING METHOD FOR MICROBEAM RADIOSURGERY

BACKGROUND

1. Field of the Invention

The present invention relates to methods for performing radiosurgery on a patient using microbeam radiation.

2. Description of the Related Art

A radiosurgery method which employs sub-millimeter beams of X-rays, termed microbeams, was patented by Slatkin et al. nearly two decades ago (see U.S. Pat. No. 5,339,347, the disclosure of which is incorporated herein by reference). Subsequent scientific studies of the effects of microbeam radiation have further illuminated Slatkin's work, showing that while the tissue cells in the direct path of a microbeam are destroyed, the region of destruction is sufficiently small in width that the adjacent undamaged tissue is capable of healing the damaged region (see Dilmanian et al., *Experimental Hematology*, Vol. 35, 2007, pp. 69-77, the disclosure of which is incorporated herein by reference). This feature of microbeam radiation, combined with proper targeting technique, promises a means to destroy diseased tissue without damaging the functionality of the surrounding normal healthy tissue.

The most successful prior art targeting technique is termed multidirectional interlaced microbeam radiation therapy (MIMRT). This technique was patented by Dilmanian et al. (see U.S. Pat. No. 7,194,063 B2, the disclosure of which is incorporated herein by reference). MIMRT is comprised of cross firing from several directions such that the diseased tissue receives dosage in a broad beam pattern while surrounding healthy tissue receives dosage in a segmented beam pattern.

As an example, referring to FIG. 1A, a body of diseased tissue 100 is targeted by three linear arrays of planar microbeams 120, 122, and 124. The direction of motion vectors for these arrays, 140, 142, and 144, respectively, are located in the same plane, XY for the coordinate system shown, and are separated in angle by 120 degrees.

Referring to FIG. 1B, each microbeam array is comprised of planes of radiation with width 180, height 182, and pitch 184. The pitch 184, in this example, is equal to three times the width 180. The height 182 is sufficiently large to span the breadth of the body of diseased tissue.

Referring again to FIG. 1A, the array 122 is displaced by one beam width 180 in the Z direction relative to the array 120. The array 124 is displaced by two beam widths 180 in the Z direction relative to the array 120.

Referring to FIG. 1C, the intersection of arrays 120, 122, and 124 at the targeted body of diseased tissue 100 is shown. The arrays 120, 122, and 124 are interlaced.

Referring to FIG. 1D, a cross section through the diseased tissue 100 is shown. Because the microbeam arrays 120, 122, and 124 are interlaced at the target body 100, the entire volume of the target body 100 is exposed to radiation. Normal tissue outside the target body 100, however, is exposed only to the segmented radiation pattern of the individual arrays. By this scheme, the diseased tissue 100 is destroyed while the functionality of the surrounding normal tissue is spared.

A serious difficulty associated with MIMRT is patient motion. The microbeam arrays 120, 122, and 124 of FIG. 1A are delivered sequentially in time. If the target body 100 moves during the time between deliveries of the respective microbeam arrays, the interlacing of damaged regions in the target body 100 does not properly occur and a broad beam damage pattern is not achieved. As such, the diseased tissue 100 is not completely destroyed. Patient motion on the order of a microbeam width compromises the effectiveness of MIMRT. Patient motion larger than this is guaranteed in practice. As an example, for a target body of diseased tissue located in the lung, MIMRT is completely ineffective.

SUMMARY

In accordance with the presently claimed invention, a method of performing microbeam radiosurgery on a patient is provided whereby opposing portions of target tissue within a patient are exposed to a flux of high energy quanta via microbeam envelopes. The microbeam envelopes are applied in multiple non-parallel orientations such that the exposed portions of the target tissue define a substantially closed volume. The tissue remaining inside is thereby denied blood flow and dies.

In accordance with one embodiment of the presently claimed invention, a method of performing microbeam radiosurgery on a patient includes: exposing first opposing portions of a target tissue, within a patient, with a first plurality of microbeam envelopes which are mutually spatially distinct and substantially mutually parallel, and have corresponding surface regions which are orthogonal to a first vector having a first vector direction; exposing second opposing portions of the target tissue with a second plurality of microbeam envelopes which are mutually spatially distinct and substantially mutually parallel, and have corresponding surface regions which are orthogonal to a second vector having a second vector direction distinct from said first vector direction; and exposing at least third opposing portions of the target tissue with a third plurality of microbeam envelopes which are mutually spatially distinct and substantially mutually parallel, and have corresponding surface regions which are orthogonal to a third vector having a third vector direction distinct from said first and second vector directions; wherein the first, second and third pluralities of microbeam envelopes comprise first, second and third pluralities of flux of high energy quanta, respectively, said quanta comprising at least one of electromagnetic radiation and material particles; and wherein the first, second and at least third opposing portions of the target tissue define a substantially closed volume.

In accordance with another embodiment of the presently claimed invention, a method of performing microbeam radiosurgery on a patient includes: exposing first opposing portions of a target tissue, within a patient, with a first plurality of microbeam envelopes which are mutually spatially distinct and substantially mutually parallel, and define a first array beam front plane; exposing second opposing portions of the target tissue with a second plurality of microbeam envelopes which are mutually spatially distinct and substantially mutually parallel, and define a second array beam front plane; and exposing at least third opposing portions of the target tissue with a third plurality of microbeam envelopes which are mutually spatially distinct and substantially mutually parallel, and define a third array beam front plane non-parallel with the first and second array beam front planes; wherein the first, second and third pluralities of microbeam envelopes comprise first, second and third pluralities of flux of high energy quanta, respectively, said quanta comprising at least one of electromagnetic radiation and material particles; and wherein the first, second and at least third opposing portions of the target tissue define a substantially closed volume.

BRIEF DESCRIPTION OF THE DRAWINGS

FIG. 2A illustrates targeting of tissue with radiation using multidirectional orthogonal microbeams in accordance with an exemplary embodiment of the presently claimed invention.

FIG. 3A illustrates targeting of tissue with radiation using multidirectional orthogonal microbeams in accordance with another exemplary embodiment of the presently claimed invention.

DETAILED DESCRIPTION

Figure 1A:
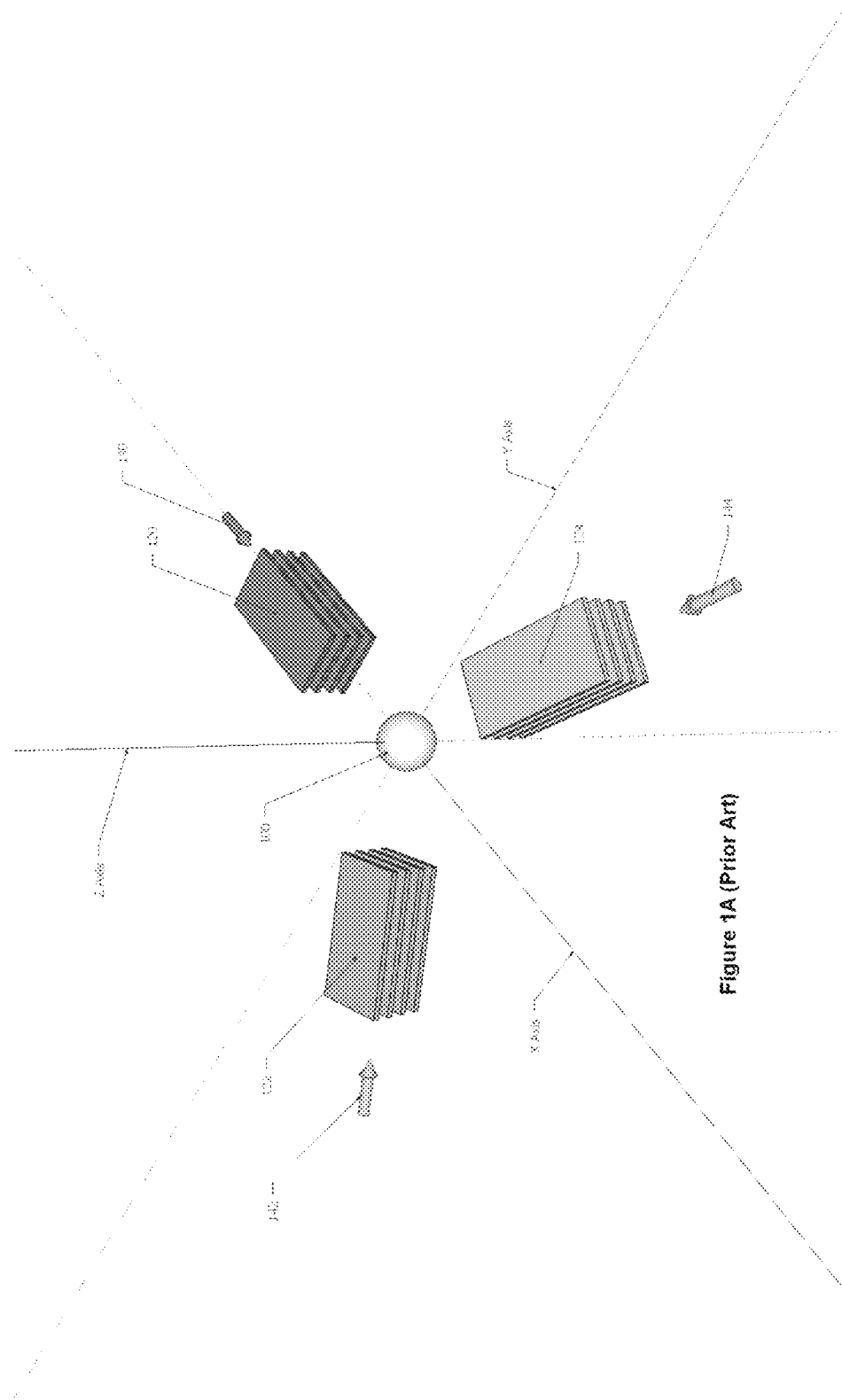
FIG. 1A illustrates targeting of tissue with radiation using conventional multidirectional interlaced microbeam radiation therapy (MIMRT).
Figure 1B:
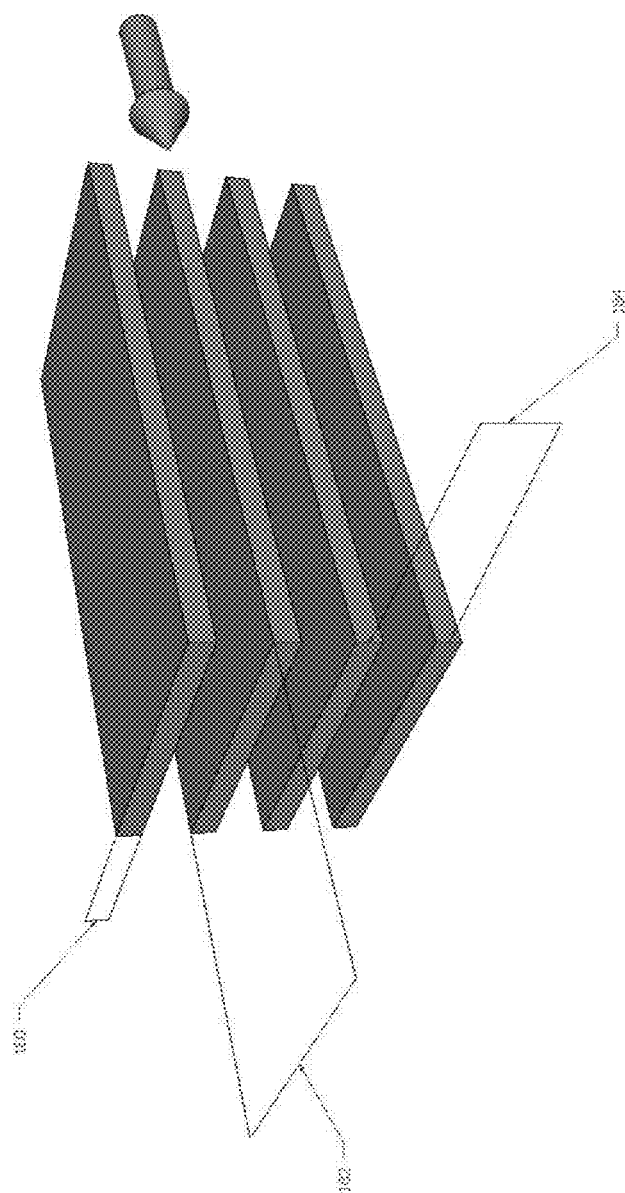
FIG. 1B illustrates MIMRT microbeam structure.
Figure 1C:
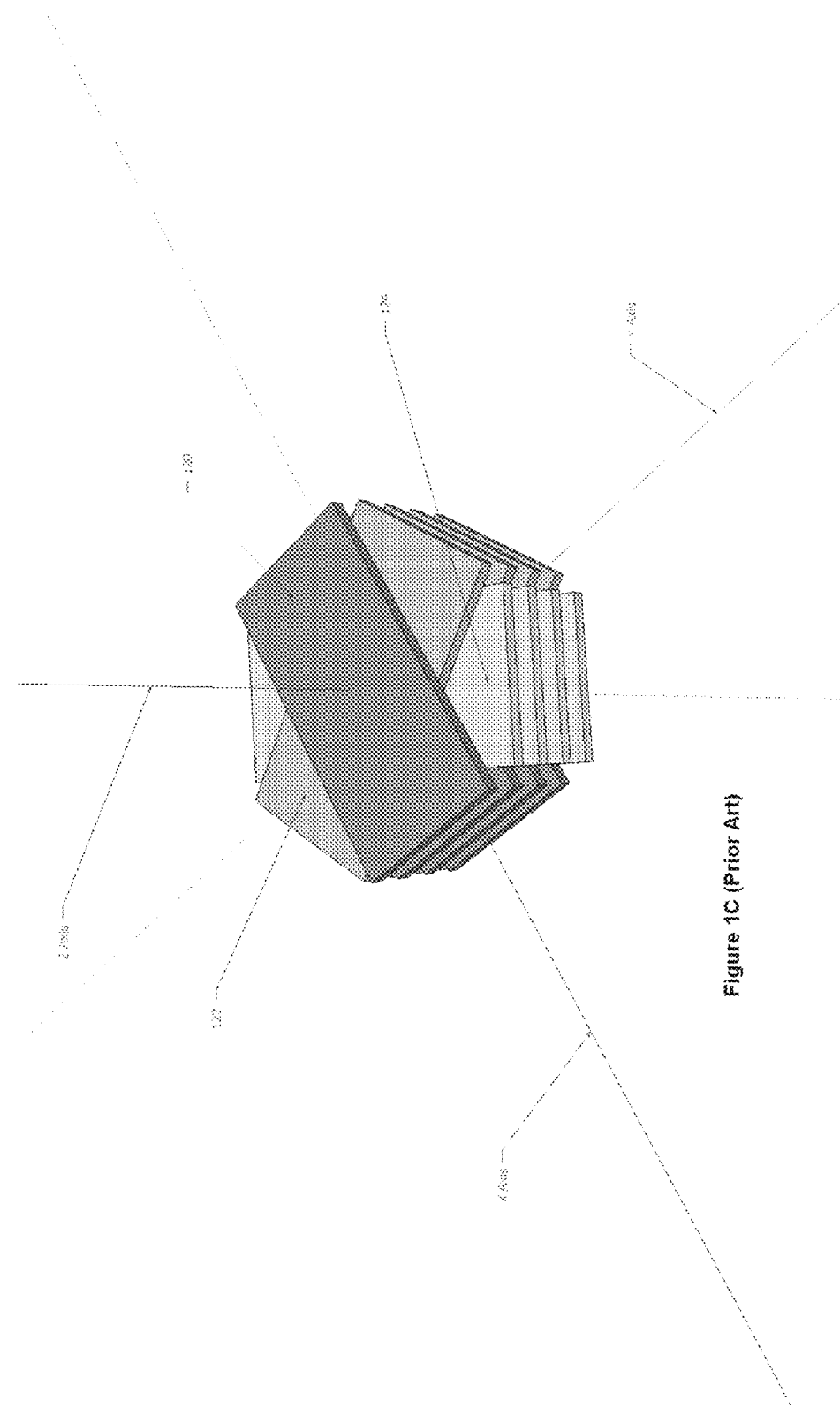
FIG. 1C illustrates interlacing of the MIMRT microbeams of FIG. 1A at the target tissue.
Figure 1D:
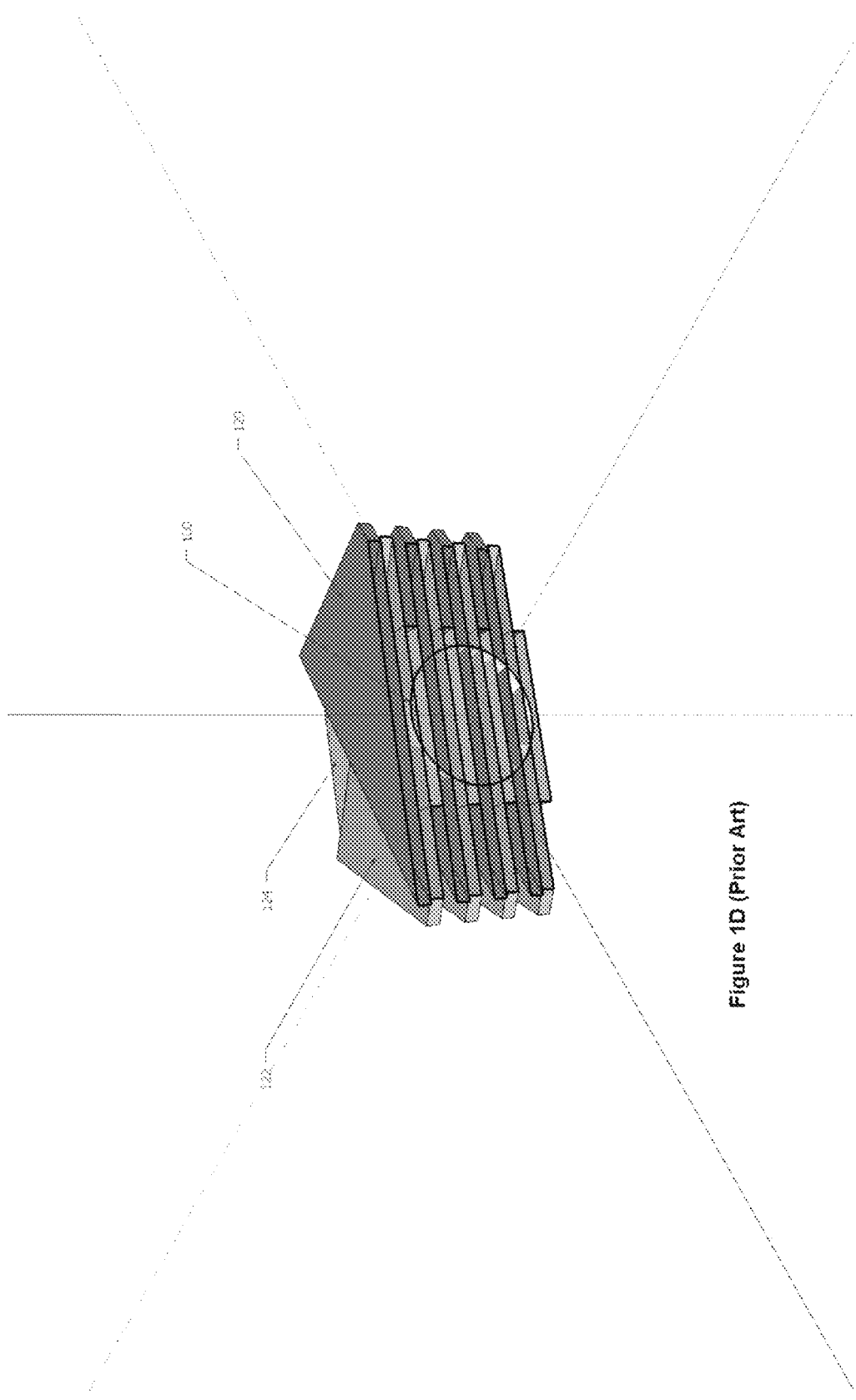
FIG. 1D illustrates a cross-section view of the interlaced MIMRT microbeams of FIG. 1A at the target tissue.

The following detailed description is of example embodiments of the presently claimed invention with references to the accompanying drawings. Such description is intended to be illustrative and not limiting with respect to the scope of the present invention. Such embodiments are described in sufficient detail to enable one of ordinary skill in the art to practice the subject invention, and it will be understood that other embodiments may be practiced with some variations without departing from the spirit or scope of the subject invention.

In accordance with exemplary embodiments of the presently claimed invention, the target body of diseased tissue is destroyed by a dicing technique rather than an interlacing technique. Each plane of microbeam radiation destroys the tissue in its path, including that of blood vessels. By arranging the planes of microbeam radiation to dice the target body into small volumes, the blood supply to these small volumes of undamaged tissue is cut off. By reason of the lack of blood supply, the tissue dies.

In accordance with one exemplary embodiment of the presently claimed invention, referring to FIG. 2A, the body of diseased tissue 100 is targeted by three linear arrays of planar microbeams 220, 222, and 224. The direction of motion vectors for these three arrays, 240, 242, and 244, respectively, are mutually orthogonal. Furthermore, the orientations of the planes of microbeam radiation associated with each array 220, 222, and 224 are mutually orthogonal. Specifically, for the coordinate system shown, the array 220 travels parallel to the X axis, and the planes of radiation are oriented orthogonal to the Y axis. The array 222 travels parallel to the Y axis, and the planes of radiation are oriented orthogonal to the Z axis. The array 224 travels parallel to the Z axis, and the planes of radiation are oriented orthogonal to the X axis.

Figure 2B:
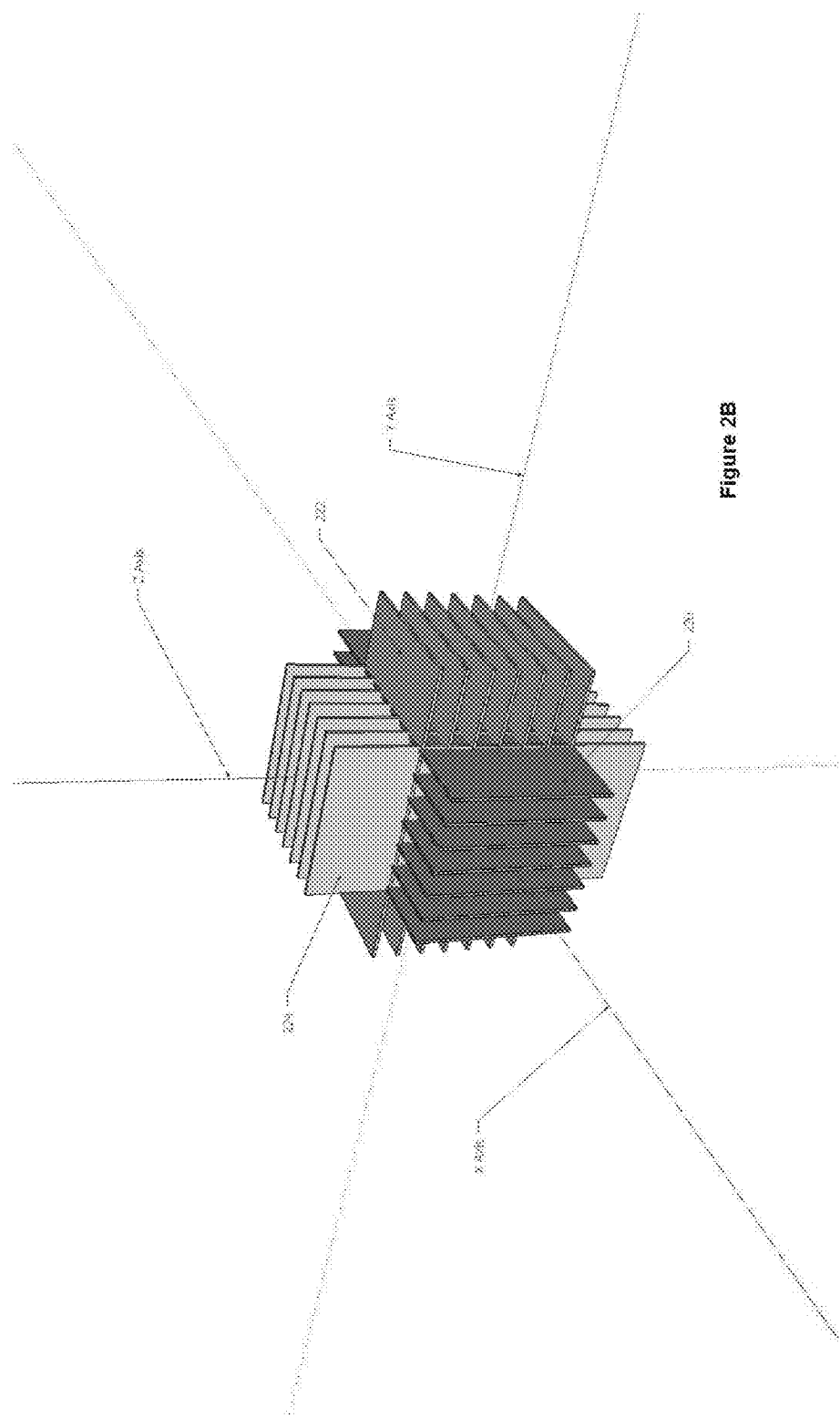
FIG. 2B illustrates an intersection of the multidirectional orthogonal microbeams of FIG. 2A at the target tissue.

Referring to FIG. 2B, the intersection of arrays 220, 222, and 224 at the targeted body of diseased tissue 100 is shown.

Figure 2C:
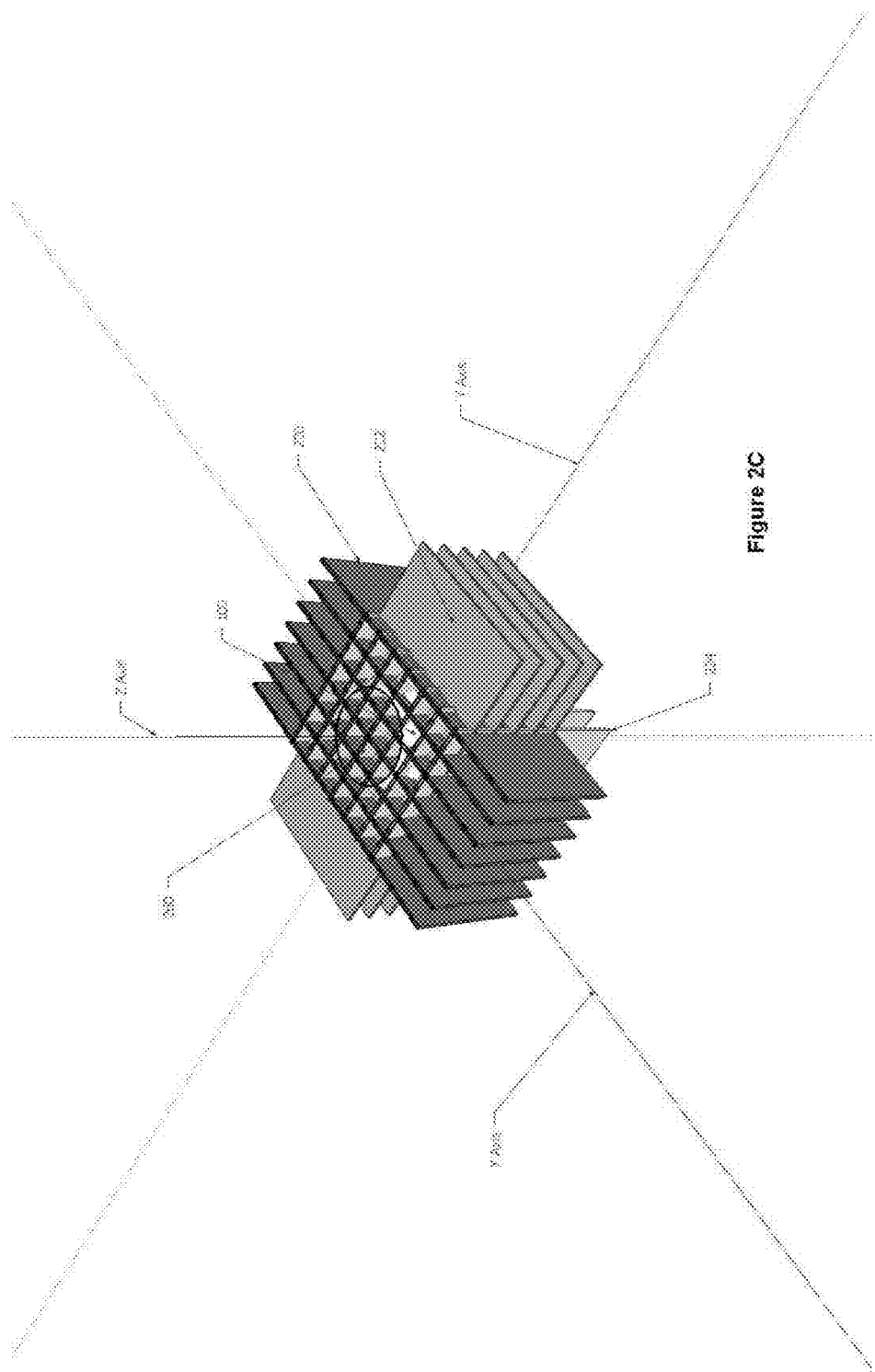
FIG. 2C illustrates a cross-section view of the multidirectional orthogonal microbeams of FIG. 2A at the target tissue.

Referring to FIG. 2C, a cross section through the diseased tissue 100 is shown. Because the planes of the microbeam arrays 220, 222, and 224 are mutually orthogonal, the entire volume of the target body 100 is diced into small rectangular volumes 260.

The success of this targeting technique is insensitive to minor target motion. The body of diseased tissue 100 can move by several microbeam widths during the delivery of the microbeam arrays 220, 222, and 224 without compromising the dicing method.

In accordance with another exemplary embodiment of the presently claimed invention, the dicing of the target body 100 is achieved by irradiating from two orthogonal directions instead of three. Referring to FIG. 3A, the body of diseased tissue 100 is targeted by three linear arrays of planar microbeams 320, 322, and 324. The direction of motion vectors 340 and 342, associated with the arrays 320 and 322, respectively, are along the same axis. The direction of motion vector 344, associated with the array 324, is orthogonal to the direction of motion vectors 340 and 342. The orientations of the planes of microbeam radiation associated with each array 320, 322, and 324 are mutually orthogonal. Specifically, for the coordinate system shown, the array 320 travels parallel to the X axis, and the planes of radiation are oriented orthogonal to the Y axis. The array 322 also travels parallel to the X axis, and the planes of radiation are oriented orthogonal to the Z axis. The array 324 travels parallel to the Z axis, and the planes of radiation are oriented orthogonal to the X axis.

Figure 3B:
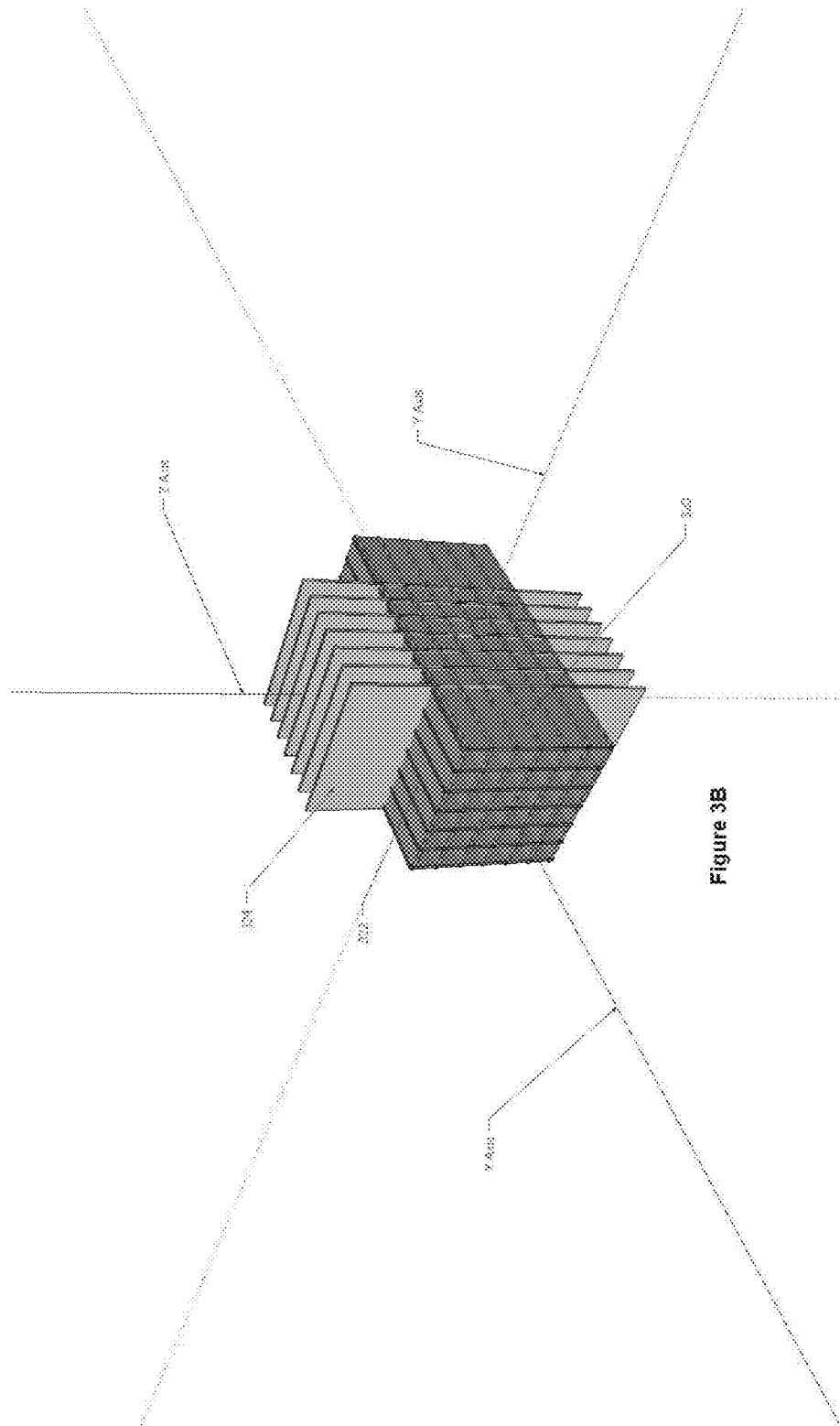
FIG. 3B illustrates an intersection of the multidirectional orthogonal microbeams of FIG. 3A at the target tissue.

Referring to FIG. 3B, the intersection of arrays 320, 322, and 324 at the targeted body of diseased tissue 100 is shown.

Figure 3C:
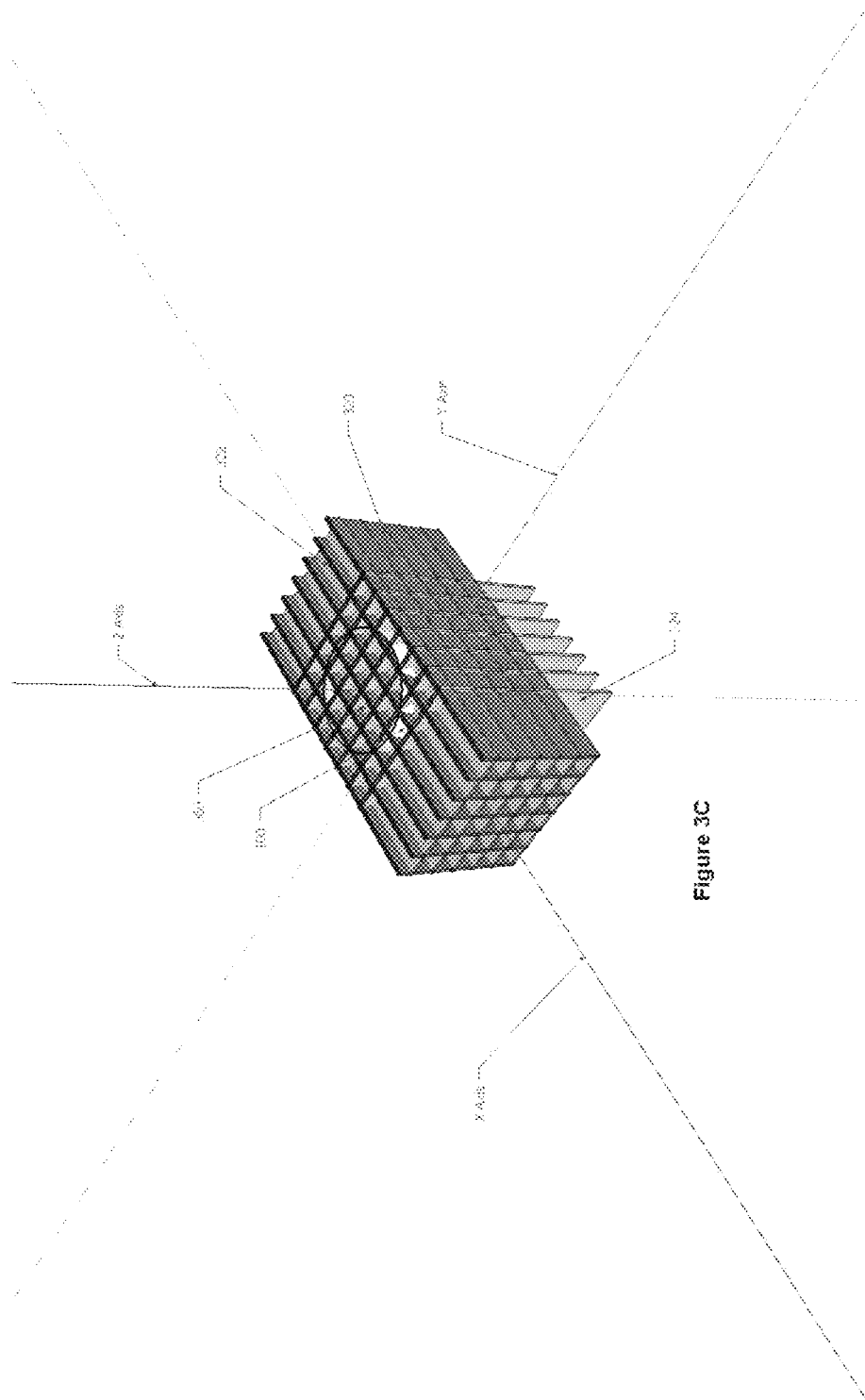
FIG. 3C illustrates a cross-section view of the multidirectional orthogonal microbeams of FIG. 3A at the target tissue.

Referring to FIG. 3C, a cross section through the diseased tissue 100 is shown. Because the planes of the microbeam arrays 320, 322, and 324 are mutually orthogonal, the entire volume of the target body 100 is diced into small rectangular volumes 360.

In accordance with other exemplary embodiments of the presently claimed invention, more than three sets of microbeam arrays may be used to dice the target body of diseased tissue into small volumes. The orientations and the directions of motion of the more than three sets of microbeam arrays need not be mutually orthogonal. In such cases, the shape of the small volumes into which the target body of diseased tissue is diced will be other than rectangular. Whatever the number of sets of microbeam arrays, their orientations, or the directions of motion, it is only necessary to dice the target body of diseased tissue into substantially closed volumes.

In accordance with other exemplary embodiments of the presently claimed invention, the microbeams need not be formed using X-rays, which comprise one type of high energy electromagnetic radiation. For example, fluxes of other types of high energy quanta can be used as well, including gamma rays, which comprise another type of high energy electromagnetic radiation, and material particles such as protons, neutrons, alpha particles, and carbon ions.

As depicted in the drawings and in accordance with exemplary embodiments, the individual microbeams have a rectangular cross-section. However, as will be readily appreciated by those skilled in the art, additional exemplary embodiments can include microbeams having other than strictly rectangular cross-sections, such as other parallelograms, trapezoids or other forms of quadrilaterals, or curvaceous cross-sections, such as elliptical. Accordingly, microbeams 220, 222, and 224 in FIG. 2A would have major axes parallel to the Z, X, and Y axes, and minor axes parallel to the Y, Z, and X axes, respectively. Similarly, microbeams 320, 322, and 324 in FIG. 3A would have major axes parallel to the Z, Y, and Y axes, and minor axes parallel to the Y, Z, and X axes, respectively. Further, other curvaceous cross-sections are possible as well, so long as the intersections of such microbeams result in at least substantially closed volumes of the targeted tissue being defined, wherein blood flow to such volumes of tissue is cut off, thereby causing such volumes of tissue to die.

Various other modifications and alterations in the structure and method of operation of this invention will be apparent to those skilled in the art without departing from the scope and the spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A method of performing microbeam radiosurgery on a patient, comprising:
    exposing first opposing portions of a target tissue, within a patient, with a first plurality of microbeam envelopes which are mutually spatially distinct and substantially mutually parallel, and have corresponding first opposing surface regions which are mutually spaced apart and orthogonal to a first vector having a first vector direction;
    exposing second opposing portions of said target tissue with a second plurality of microbeam envelopes which are mutually spatially distinct and substantially mutually parallel, and have corresponding second opposing surface regions which are mutually spaced apart and orthogonal to a second vector having a second vector direction distinct from said first vector direction; and
    exposing at least third opposing portions of said target tissue with a third plurality of microbeam envelopes which are mutually spatially distinct and substantially mutually parallel, and have corresponding third opposing surface regions which are mutually spaced apart and orthogonal to a third vector having a third vector direction distinct from said first and second vector directions;
    wherein said first, second and third pluralities of microbeam envelopes comprise first, second and third pluralities of flux of high energy quanta, respectively, said quanta comprising at least one of electromagnetic radiation and material particles; and
    wherein said first, second and at least third opposing surface regions of said first, second and third pluralities of microbeam envelopes, respectively, define a substantially closed volume.

2. The method of claim 1, wherein said first and second vector directions are substantially mutually orthogonal.

3. The method of claim 1, wherein said first, second and third vector directions are substantially mutually orthogonal.

4. The method of claim 1, wherein said exposing first opposing portions of a target tissue, said exposing second opposing portions of said target tissue and said exposing at least third opposing portions of said target tissue comprise exposing said first, second and at least third opposing portions of said target tissue sequentially.

5. The method of claim 1, wherein said exposing first opposing portions of a target tissue, said exposing second opposing portions of said target tissue and said exposing at least third opposing portions of said target tissue comprise exposing at least two of said first, second and at least third opposing portions of said target tissue simultaneously.

6. The method of claim 1, wherein:
    said exposing first opposing portions of a target tissue comprises exposing said first opposing portions of said target tissue from a first exposure direction;
    said exposing second opposing portions of said target tissue comprises exposing said second opposing portions of said target tissue from a second exposure direction distinct from said first exposure direction; and
    said exposing at least third opposing portions of said target tissue comprises exposing said at least third opposing portions of said target tissue from at least a third exposure direction distinct from said first and second exposure directions.

7. The method of claim 6, wherein said first, second and third exposure directions are substantially mutually orthogonal.

8. The method of claim 1, wherein:
    said exposing first opposing portions of a target tissue comprises exposing said first opposing portions of said target tissue from a first exposure direction;
    said exposing second opposing portions of said target tissue comprises exposing said second opposing portions of said target tissue from said first exposure direction; and
    said exposing at least third opposing portions of said target tissue comprises exposing said third opposing portions of said target tissue from a second exposure direction distinct from said first exposure direction.

9. The method of claim 8, wherein said first and second exposure directions are substantially mutually orthogonal.

10. The method of claim 1, wherein at least one of said first, second and third pluralities of microbeam envelopes has a quadrilateral cross-section.

11. The method of claim 1, wherein at least one of said first, second and third pluralities of microbeam envelopes has a curvaceous cross-section.

12. A method of performing microbeam radiosurgery on a patient, comprising:
    exposing first opposing portions of a target tissue, within a patient, with a first plurality of microbeam envelopes which
        are mutually spatially distinct and substantially mutually parallel,
        define a first array beam front plane, and
        have corresponding first opposing surface regions which are mutually spaced apart and orthogonal to said first array beam front plane;
    exposing second opposing portions of said target tissue with a second plurality of microbeam envelopes which
        are mutually spatially distinct and substantially mutually parallel,
        define a second array beam front plane, and
        have corresponding second opposing surface regions which are mutually spaced apart and orthogonal to said second array beam front plane; and
    exposing at least third opposing portions of said target tissue with a third plurality of microbeam envelopes which
        are mutually spatially distinct and substantially mutually parallel,
        define a third array beam front plane non-parallel with said first and second array beam front planes, and
        have corresponding third opposing surface regions which are mutually spaced apart and orthogonal to said third array beam front plane;
    wherein said first, second and third pluralities of microbeam envelopes comprise first, second and third pluralities of flux of high energy quanta, respectively, said quanta comprising at least one of electromagnetic radiation and material particles; and
    wherein said first, second and at least third opposing surface regions of said first, second and third pluralities of microbeam envelopes, respectively, define a substantially closed volume.

13. The method of claim 12, wherein said first, second and third array beam front planes are substantially mutually orthogonal.

14. The method of claim 12, wherein said first and second array beam front planes are substantially orthogonal to said third array beam front plane.

15. The method of claim 12, wherein said exposing first opposing portions of a target tissue, said exposing second opposing portions of said target tissue and said exposing at least third opposing portions of said target tissue comprise exposing said first, second and at least third opposing portions of said target tissue sequentially.

16. The method of claim 12, wherein said exposing first opposing portions of a target tissue, said exposing second opposing portions of said target tissue and said exposing at least third opposing portions of said target tissue comprise exposing at least two of said first, second and at least third opposing portions of said target tissue simultaneously.

17. The method of claim 12, wherein:
said exposing first opposing portions of a target tissue comprises exposing said first opposing portions of said target tissue from a first exposure direction;
said exposing second opposing portions of said target tissue comprises exposing said second opposing portions of said target tissue from a second exposure direction distinct from said first exposure direction; and
said exposing at least third opposing portions of said target tissue comprises exposing said at least third opposing portions of said target tissue from at least a third exposure direction distinct from said first and second exposure directions.

18. The method of claim 17, wherein said first, second and third exposure directions are substantially mutually orthogonal.

19. The method of claim 12, wherein:
said exposing first opposing portions of a target tissue comprises exposing said first opposing portions of said target tissue from a first exposure direction;
said exposing second opposing portions of said target tissue comprises exposing said second opposing portions of said target tissue from said first exposure direction; and
said exposing at least third opposing portions of said target tissue comprises exposing said third opposing portions of said target tissue from a second exposure direction distinct from said first exposure direction.

20. The method of claim 19, wherein said first and second exposure directions are substantially mutually orthogonal.

21. The method of claim 12, wherein at least one of said first, second and third pluralities of microbeam envelopes has a quadrilateral cross-section.

22. The method of claim 12, wherein at least one of said first, second and third pluralities of microbeam envelopes has a curvaceous cross-section.

* * * * *